United States Patent [19]

Kayal et al.

[11] Patent Number: 5,711,875
[45] Date of Patent: *Jan. 27, 1998

[54] CELL STRAINER CAP

[75] Inventors: John J. Kayal, Wayne, N.J.; Seiji Fukushima, Chiba, Japan; Thomas Fleming, St. Paul, Minn.

[73] Assignee: Becton Dickinson and Company, Franklin Lakes, N.J.

[*] Notice: The term of this patent shall not extend byeond the expiration date of Pat. No. 5,518,612.

[21] Appl. No.: 763,599

[22] Filed: Dec. 11, 1996

Related U.S. Application Data

[62] Division of Ser. No. 565,468, Nov. 30, 1995, Pat. No. 5,601,728.

[51] Int. Cl.⁶ ............................................. B01D 29/085
[52] U.S. Cl. .................... 210/232; 210/232; 210/452; 210/467; 210/469; 210/474; 210/513; 422/101
[58] Field of Search .................... 210/474, 477, 210/495, 232, 238, 248, 451, 452, 454, 464, 466, 467, 469, 473, 475, 476, 508; 422/99, 101, 102

[56] References Cited

U.S. PATENT DOCUMENTS

| | | | |
|---|---|---|---|
| 2,673,649 | 3/1954 | Bass, Sr. | 210/471 |
| 2,839,056 | 6/1958 | Mailly. | |
| 3,651,947 | 3/1972 | Schollhamer | 210/474 |
| 3,788,484 | 1/1974 | Godin | 210/470 |
| 4,075,105 | 2/1978 | Steiner et al. | 210/477 |
| 4,131,549 | 12/1978 | Ferrara | 210/359 |
| 4,468,321 | 8/1984 | St. John | 210/232 |
| 5,169,524 | 12/1992 | Meiritz et al. | 210/232 |
| 5,391,496 | 2/1995 | Kayal et al. | 435/286 |
| 5,518,612 | 5/1996 | Kayal et al. | 210/232 |
| 5,601,728 | 2/1997 | Kayal et al. | 210/768 |

*Primary Examiner*—W. L. Walker
*Attorney, Agent, or Firm*—Bruce S. Weintraub

[57] ABSTRACT

A cell strainer assembly useful for filtering and collecting suspensions for use in immunological studies and more particularly in flow cytometry procedures. The assembly comprises a container and a cap with means for filtering and collecting a suspension.

1 Claim, 5 Drawing Sheets

CELL STRAINER CAP

This is a divisional of application Ser. No. 08/565,468, filed on Nov. 30, 1995, which is now U.S. Pat. No. 5,601,728.

BACKGROUND OF THE INVENTION

1. Field of the Invention

This invention relates to a cell strainer assembly and its method of use. More particularly, the invention relates to a cell strainer cap and container suitable for filtering and collecting suspensions for use in immunological studies and more particularly in flow cytometry procedures.

2. Description of Related Art

Suspensions containing lymphocytes require preparation for immunological study purposes. These suspensions typically contain impurities, such as supporting tissue and spiculae that must be removed from the suspension.

Conventionally, these impurities are collected by filtrating the suspensions with gauze. However, the recovery rate of a useful suspension by using gauge is very low. The recovery rate of a filtrate is low because a portion of the liquid of the filtrate is absorbed by gauze. Gauze material readily absorbs liquids.

Therefore, a special need exists for a device and method for straining suspensions for use in immunological studies.

SUMMARY OF THE INVENTION

The present invention is a cell strainer assembly comprising a cap and a container. The cap preferably comprises a top portion, a bottom portion, an annular skirt extending from the top portion to the bottom portion having an inner surface and an outer surface, and an orifice in the top portion that comprises means for filtering a suspension.

The cap preferably further includes an inner inverted skirt portion surrounded by the inner surface of the annular skirt. The compartment area extends from the top portion to an orifice at a bottom surface that comprises means for filtering a suspension. Most preferably, the inner inverted skirt portion is separated from the inner surface of the annular skirt by an annular space. Desirably, the inside surface of the annular skirt and the inner inverted skirt each comprise at least one protrusion. The cap may further comprise a rim extending from the outer surface of the annular skirt.

The container preferably comprises an open top portion, a closed bottom portion and a sidewall extending from the top portion to the bottom portion. Preferably, the container may also include an annular locking ring portion located on the outer surface of the top portion of the container.

Preferably, the cap and the container are removably secured wherein the inner surfaces of the cap interact with the top portion of the container, whereby the annular space of the cap receives the top portion of the container and the protrusions of the inner inverted skirt bear against the inner surface of the top portion of the container and the protrusions of the annular skirt bear against the outer surface of the top portion of the container below the locking ring portion.

Most preferably, the means for filtering a suspension is a filter component made of a nylon mesh material and having a pore size of about 30 to about 200 microns.

Preferably, the inverted skirt portion of the cap is sized and shaped in such a way to provide a filtered suspension directly into a tube.

The cell strainer cap and tube assembly of the present invention provides a self-contained unit readily available to dissociate clumped cells in preparation for cell counting or flow cytometry.

Preferably, the cell strainer cap is used in conjunction with a tube, such as the FALCON® 2235 12×75 mm tube (trademark of Becton, Dickinson and Company, Franklin Lakes, N.J. 07417-1880) to simplify DNA sample preparation. Most preferably, the cell strainer cap and tube can be used in conjunction with a flow cytometer such as the FACSscan™ Flow Cytometer (trademark of Becton, Dickinson and Company, Franklin Lakes, N.J. 07417-1880) for DNA analysis.

Advantages of using a cell strainer assembly of the present invention include simplifying DNA sample preparation, eliminating the need to cut and manipulate nylon mesh to filter samples, directing filtration through the cell strainer cap and into a tube and easy disposal of used cell strainer cap thereby minimizing exposure to filtered materials.

Most preferably, the assembly of the present invention may be used to remove impurities such as supporting tissues, spicular, etc. from a suspension containing lymphocytes when such a suspension is to be prepared for immunological studies and the lymphocyte to be used for cell fusion.

The cell strainer assembly of the present invention may be used to remove supporting tissues and cell packets when a single cell suspension is prepared from various organs; to remove products of cytolysis and cell packets when isolated cell groups are obtained from cultured cells; and to filtrate various liquid samples.

Further advantages of the present invention include, the nylon filter material of about 30 to about 200 microns does not wrinkle; the nylon filter material can be used at room temperature; the cell strainer cap easily mates with a collection tube, as well as being easily removed; use of a cell strainer cap prevents contamination of the sample as it is prepared and collected in the tube; and the entire assembly may be sterilized.

DETAILED DESCRIPTION

Figure 1:
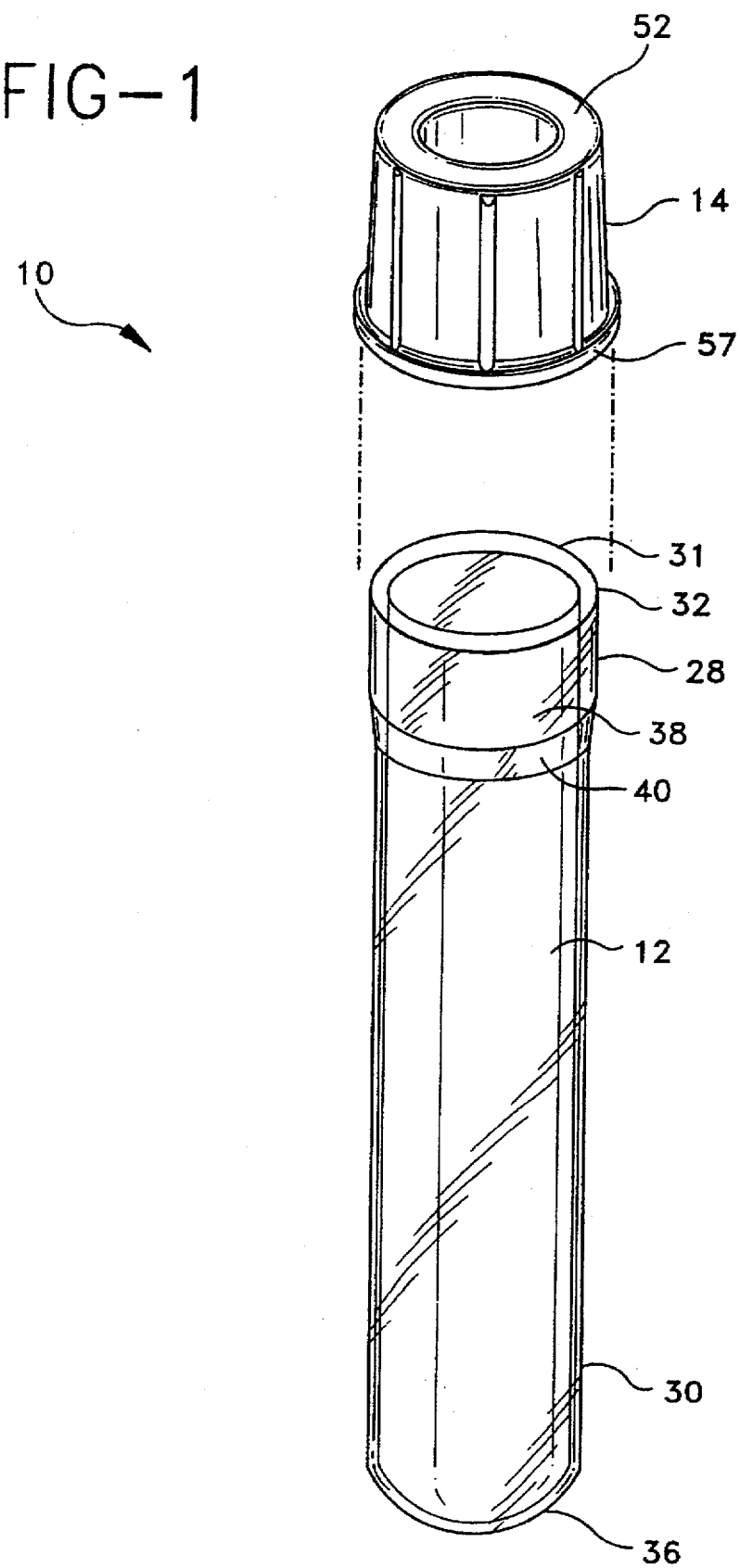
FIG. 1 is a perspective view of the assembly illustrating the container and the cap.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
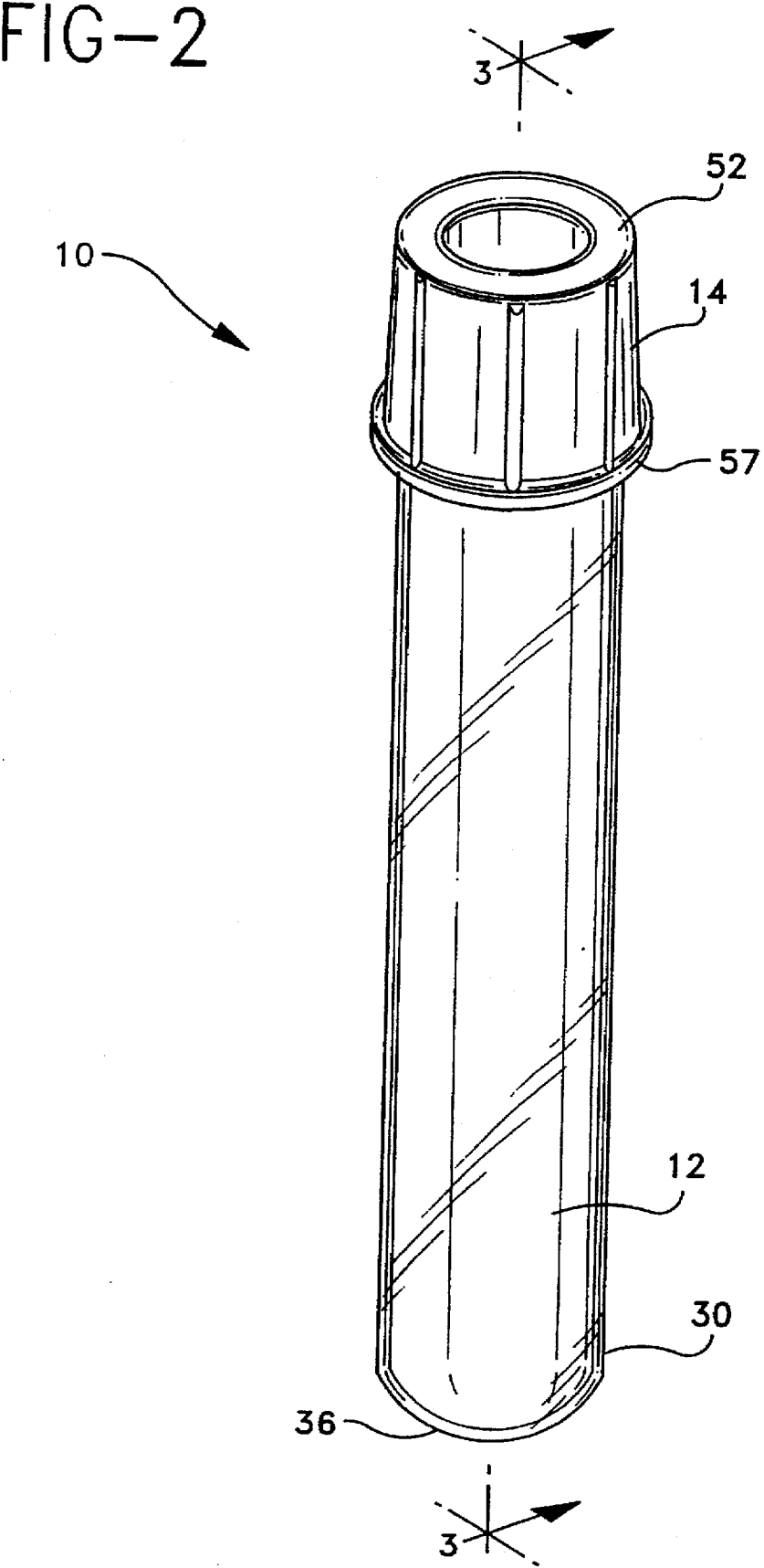
FIG. 2 is a perspective view of the assembly illustrating the container with the cap mated.

Referring to the drawings in which like reference characters refer to like parts throughout the several view thereof, FIGS. 1 and 2 illustrate a cell strainer assembly 10 comprising a container 12, and a cap or closure 14. The container is preferably made from impact resistant plastic or glass which is gas impermeable, optically clear, non-toxic and inert with respect to the suspension materials.

Figure 3:
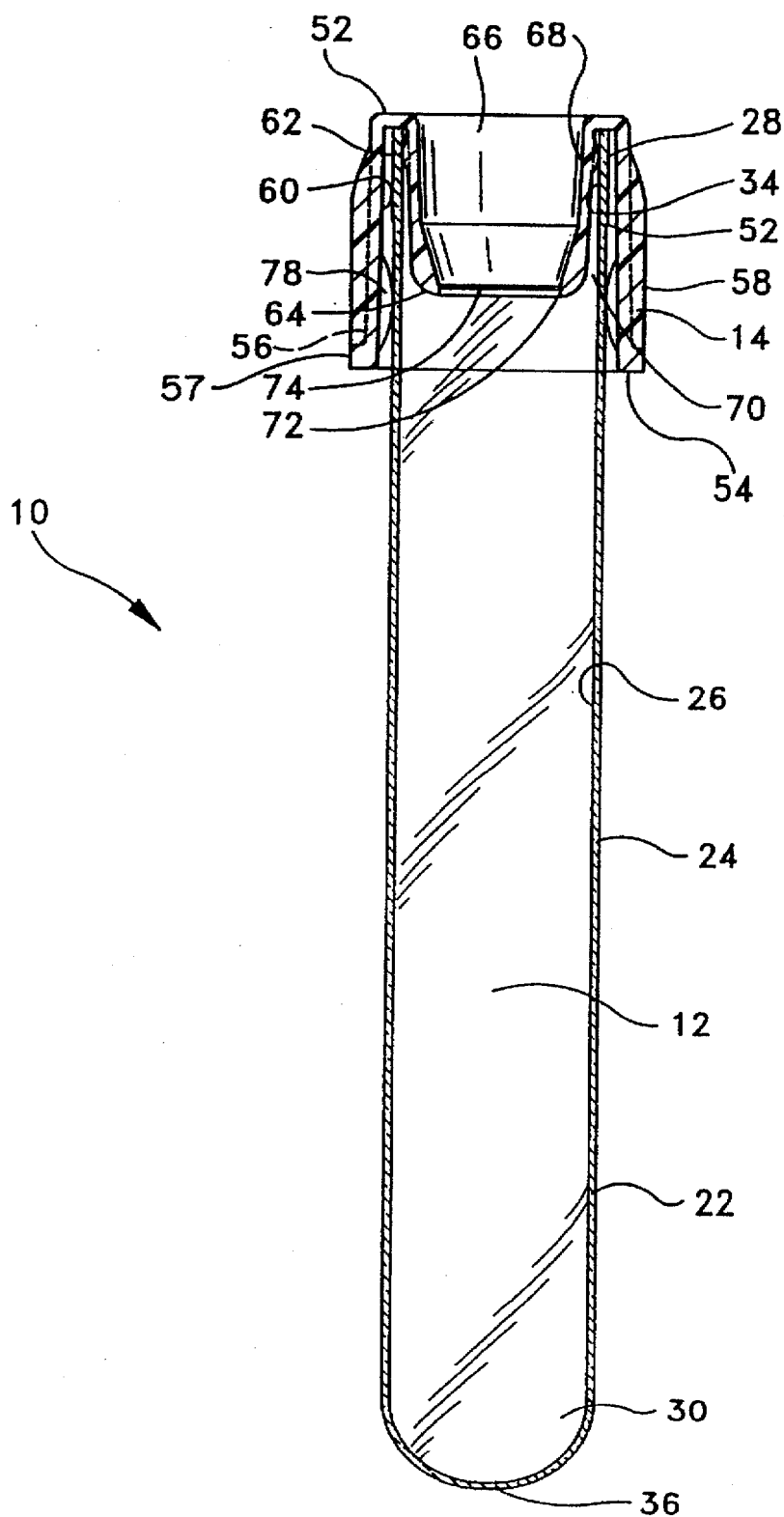
FIG. 3 is a cross sectional view of the container and cap of FIG. 2 taken along line 3—3 thereof.
Figure 4:
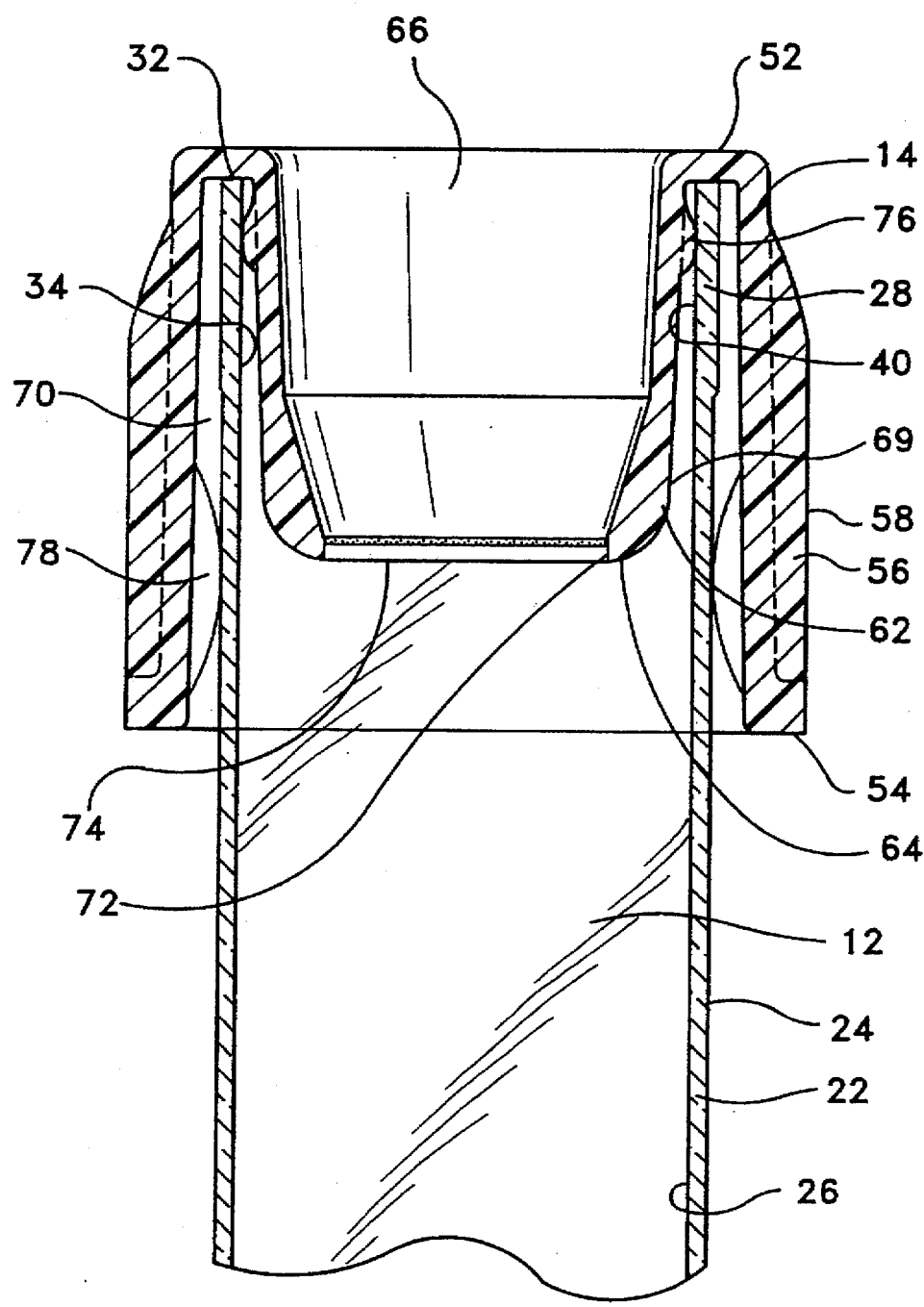
FIG. 4 is an enlarged cross sectional view of the container and cap of FIG. 2, taken along line 3—3 thereof.
Figure 5:
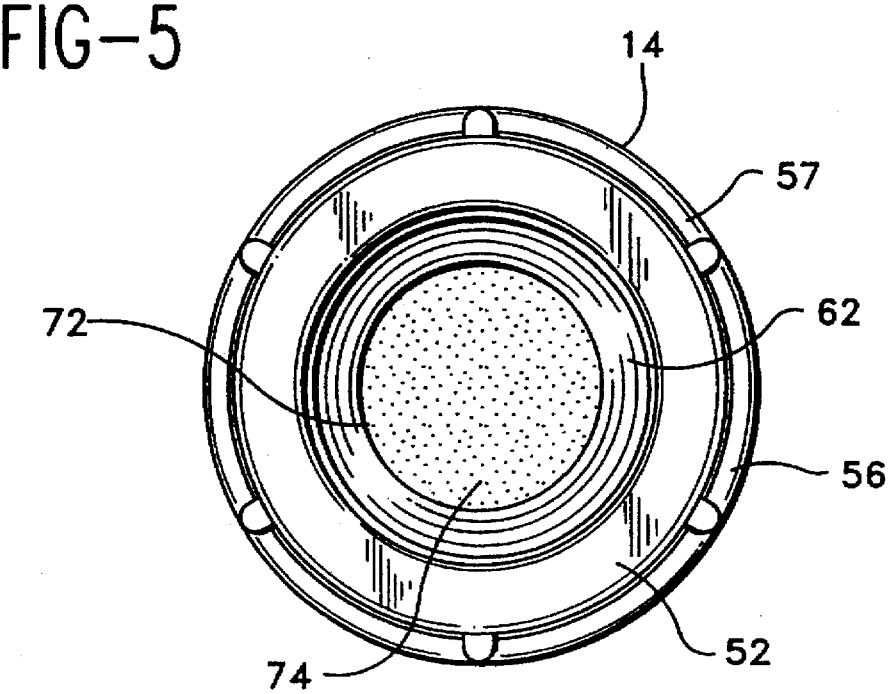
FIG. 5 is a top view of the cap of FIG. 1.
Figure 6:
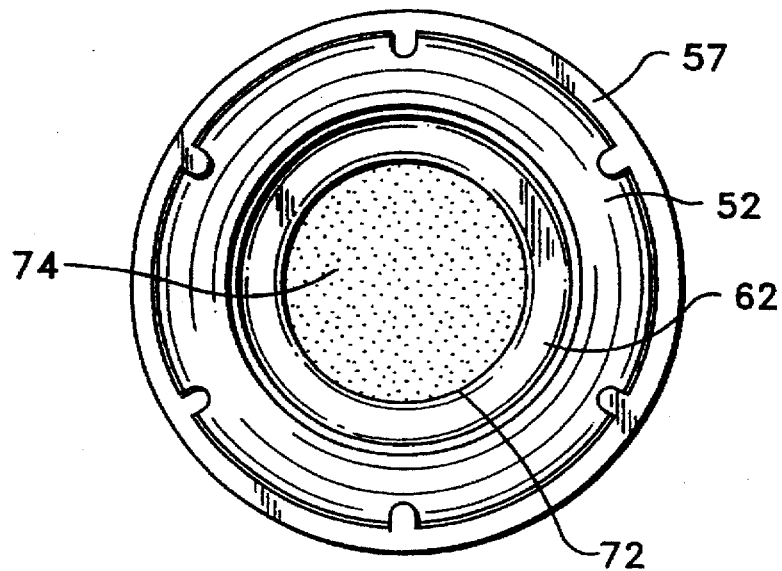
FIG. 6 is a bottom view of the cap of FIG. 1.

As illustrated in FIGS. 3 and 4, container 12 has a sidewall 22 having an outer surface 24 and an inner surface 26. The sidewall extends from an upper portion 28 to a lower portion 30. Upper portion 28 includes a top edge 32 and an inner surface 34 and lower portion 30 includes a rounded closed end 36.

As shown in FIGS. 3 and 4, further positioned on the outer surface of the upper portion of the container is an annular locking and/or sealing ring 38. The locking ring extends from top edge 32 to a lower edge 40.

As shown in FIG. 3, cap 14 has a top surface 52, a bottom stop ledge 54, an annular outer skirt 56 extending from the top surface to the bottom stop ledge and a rim 57 extending from the annular skirt. The annular outer skirt has an outer wall surface 58 and an inner wall surface 60. Cap 14 further includes an inner annular inverted recessed skirt portion or cup 62 that extends from top surface 52 to a bottom surface 64. The sidewall 68 of the cup decreases in circumference as it extends from the top surface to the bottom surface. The inverted recessed skirt portion defines a compartment area 66 on the top surface of the cap for receiving a fluid sample.

The inner wall surface of the annular outer skirt and the inner annular inverted recessed skirt are spaced from each other to define an annular space 70. The cap further includes an orifice 72 in bottom surface 64 of the inverted recessed skirt portion. A filter component 74 is attached to the orifice. The orifice of the cap is sized and shaped to properly support the filtering of suspension into the container.

The filter component 74 may be made from a nylon net material having a pore size of about 30 to about 200 microns. The filter mesh material is capable of removing impurities from samples such as supporting tissues, spiculae, or the like from a suspension containing lymphocytes as a large volume of filtrate to be processed is not absorbed by a filter mesh, as the filter mesh itself does not absorb water.

The outer sidewall 69 of inner annular skirt portion 62 includes a plurality of space protrusions 76 for sealing against inner surface 34 of upper portion 28 of container 12. On the inner wall surface of skirt 56 of cap 14, a plurality of circumferential space protrusions 78 are positioned to engage in snap-lock engagement with the annular sealing ring 38 positioned on the upper portion 28 of the container.

As shown in FIGS. 3 and 4, when cap 14 is removably secured to container 12, space 70 of the cap receives the upper portion of the container, protrusions 78 bear against the outer surface 24 of the container below lower edge 40 of annular sealing ring 38 and protrusions 76 bear against inner surface 34 of the container so as to form a non-permanent lock.

The device of the present invention prepares a specimen for analysis while minimizing the number of cells that are not recovered during filtration. In particular, the device of the present invention can be used to prepare a specimen for analysis in a flow cytometer. The flow cytometer is a fluorescent activated cell analyzer.

The cell strainer assembly of the present invention may be used for: supporting tissues and cell packets to be removed when a single cell suspension is prepared from various organs; removing products of cytolysis and cell packets when isolated cell groups are obtained from cultured cells; and filtering various liquid samples into a collection tube.

Cell suspensions samples can be prepared from various organs and cultured cells using different methods. When a sample liquid is poured or pipetted into a cell strainer cap, a high recovery ration and a single cell suspension are obtained.

Samples that can be prepared are single cell suspension of blood cells from bone marrow, spleen, thymus, tonsil, lymph node, etc.; cultured cell samples for cryopreservation; immunogenic cell samples; and removal of agglutinated proteins to be developed in inactivated serum.

The assembly of the present invention may be made of a clear molded thermoplastic material so that the suspensions collected may be readily viewed. Representative materials include, for example, polyethylene, polypropylene and polyvinyl chloride.

Although it is within the purview of the invention to provide caps which are colored to define specific forms of specimen containers containing materials for one reason or another or for defining the kind of examination to be conducted on the specimen collected, transparent caps may be provided. Also, it should be noted that the dimension of the container are such as to provide space for labeling which may be important for identifying the collected specimens.

EXAMPLE 1

Comparison of Nylon Mesh Material and Gauze Material

Nylon mesh material and gauze material were examined and compared using a normal saline solution. The results are reported in Table 1.

TABLE 1

| Liquid Volume (ml) | Nylon mesh material (200 mesh) | | | 2 Sheets of 2 × 30 mesh gauze (50 mesh) | | |
|---|---|---|---|---|---|---|
| | Recovered Liquid Volume (ml) | Mean (ml) | Recovery Ratio (%) | Recovered Liquid Volume (ml) | Mean (ml) | Recovery Ratio (%) |
| 50 | 49.98 | 49.87 | 99.7 | 48.00 | 47.01 | 94.02 |
| | 49.68 | ± 0.11 | ± 0.23 | 46.84 | ± 0.58 | ± 0.16 |
| | 49.90 | | | 46.61 | | |
| | 49.92 | | | 47.00 | | |
| | 49.89 | | | 46.58 | | |
| 40 | 39.90 | 39.93 | 99.8 | 36.82 | 37.11 | 92.78 |
| | 39.85 | ± 0.05 | ± 0.13 | 36.85 | ± 0.40 | ± 0.99 |
| | 39.85 | | | 36.85 | | |
| | 39.97 | | | 37.23 | | |
| | 39.96 | | | 36.90 | | |
| | 39.95 | | | 37.76 | | |
| 30 | 29.95 | 29.93 | 99.8 | 27.50 | 27.70 | 92.33 |
| | 29.99 | ± 0.06 | ± 0.19 | 27.89 | ± 0.40 | ± 1.33 |
| | 29.84 | | | 27.50 | | |

TABLE 1-continued

| | Nylon mesh material (200 mesh) | | | 2 Sheets of 2 × 30 mesh gauze (50 mesh) | | |
|---|---|---|---|---|---|---|
| Liquid Volume (ml) | Recovered Liquid Volume (ml) | Mean (ml) | Recovery Ratio (%) | Recovered Liquid Volume (ml) | Mean (ml) | Recovery Ratio (%) |
| 20 | 29.92<br>29.88<br>19.98<br>19.98<br>19.97<br>19.67<br>19.87 | 19.89<br>± 0.13 | 99.5<br>± 0.74 | 27.30<br>28.30<br>18.08<br>18.40<br>18.75<br>17.00<br>16.70 | 17.79<br>± 0.89 | 88.95<br>± 4.47 |
| 10 | 9.95<br>9.90<br>9.91<br>9.80<br>9.97 | 9.91<br>± 0.07 | 99.1<br>± 0.66 | 8.93<br>9.30<br>9.08<br>8.20<br>8.95<br>7.22<br>8.10 | 8.54<br>± 0.73 | 85.4<br>± 7.35 |
| 5 | 4.81<br>4.97<br>4.93<br>4.99<br>4.91 | 4.92<br>± 0.07 | 98.4<br>± 0.14 | 4.21<br>4.06<br>3.99<br>4.30<br>4.11 | 4.13<br>± 0.12 | 82.68<br>± 2.45 |
| 4 | 3.92<br>3.93<br>3.95<br>3.98<br>3.90 | 3.94<br>± 0.03 | 98.4<br>± 0.76 | 2.90<br>3.20<br>3.15<br>3.42<br>3.06 | 3.15<br>± 0.19 | 78.75<br>± 4.77 |
| 3 | 2.92<br>2.91<br>2.91<br>2.97<br>2.95 | 2.93<br>± 0.03 | 97.7<br>± 0.89 | 2.32<br>2.27<br>2.27<br>2.17<br>2.10 | 2.23<br>± 0.09 | 74.33<br>± 2.97 |
| 2 | 1.82<br>1.98<br>1.94<br>1.96<br>1.96 | 1.93<br>± 0.06 | 96.6<br>± 3.21 | 1.40<br>1.21<br>1.28<br>1.33<br>1.38 | 1.32<br>± 0.08 | 66.20<br>± 3.51 |
| 1 | 0.91<br>0.95<br>0.97<br>0.99<br>0.94 | 0.95<br>± 0.03 | 95.2<br>± 3.03 | 0.71<br>0.54<br>0.57<br>0.59<br>0.53<br>0.63 | 0.60<br>± 0.07 | 60.00<br>± 6.68 |

EXAMPLE 2

Comparison of Nylon Mesh Material and Gauze Material

Nylon mesh material and gauze material were examined and compared of cells using thymic lymphocytes. The results are reported in Table 2.

TABLE 2

| Cell Concentration | Nylon flesh material (200 mesh) | 2 Sheets of Gauze (50 mesh) |
|---|---|---|
| 1 × 10$^8$ cell/ml | 98.2%<br>93.5%<br>100.0%<br>100.0% | 87.8%<br>92.6%<br>90.1%<br>99.2% |
| mean | 97.9% ± 3.1 | 92.5% ± 4.9 |
| 1 × 10$^7$ cell/ml | 97.0%<br>100.0%<br>100.0%<br>100.0% | 97.8%<br>92.8%<br>88.5%<br>90.2% |
| mean | 99.4% ± 1.3 | 92.3% ± 4.1 |
| 1 × 10$^6$ cell/ml | 100.0%<br>95.8%<br>97.1% | 100.0%<br>94.4%<br>95.7% |

TABLE 2-continued

| Cell Concentration | Nylon flesh material (200 mesh) | 2 Sheets of Gauze (50 mesh) |
|---|---|---|
| mean | 100.0%<br>98.2 ± 2.1 | 98.8%<br>97.2% ± 2.6 |
| total mean | 98.5% ± 2.2 | 94.0% ± 4.3 |

What is claimed is:

1. A cell strainer cap for filtering suspensions comprising: a top portion, a bottom portion, an annular skirt extending from said top portion to said bottom portion and having an inner surface and outer surface, and inner surface inverted skirt portion surrounded by said inner surface of said annular skirt and extending from said top portion toward said bottom portion, an annular space between said inner surface of said annular skirt and said inverted skirt portion, and orifice in said bottom portion of said inverted skirt portion; means for filtering a suspension covering said orifice and protrusions on said inner surface of said annular skirt and said inverted skirt portion.

* * * * *